(12) United States Patent
Han

(10) Patent No.: US 9,226,537 B1
(45) Date of Patent: Jan. 5, 2016

(54) EYELASH MEASURING DEVICE

(71) Applicant: Yongho Han, Woodbury, NY (US)

(72) Inventor: Yongho Han, Woodbury, NY (US)

(\*) Notice: Subject to any disclaimer, the term of this patent is extended or adjusted under 35 U.S.C. 154(b) by 125 days.

(21) Appl. No.: 14/166,484

(22) Filed: Jan. 28, 2014

(51) Int. Cl.
*A61B 1/00* (2006.01)
*A61B 5/103* (2006.01)
*A61B 5/117* (2006.01)
*G01B 1/00* (2006.01)
*A41G 5/02* (2006.01)
*A61B 5/107* (2006.01)

(52) U.S. Cl.
CPC . *A41G 5/02* (2013.01); *A61B 5/107* (2013.01); *A61B 5/1072* (2013.01); *A61B 5/1076* (2013.01)

(58) Field of Classification Search
CPC ..... A61B 5/1072; A61B 5/107; A61B 5/1076
USPC .................................. 33/512, 511; 132/319
See application file for complete search history.

(56) References Cited

U.S. PATENT DOCUMENTS

| 1,890,628 | A | * | 12/1932 | Sueta et al. | 132/319 |
| 3,050,860 | A | | 8/1962 | Kosh | |
| 3,200,823 | A | | 8/1965 | Sebastian | |
| 3,517,673 | A | * | 6/1970 | Kim | 132/214 |
| 3,557,653 | A | | 1/1971 | Kim | |
| 4,660,295 | A | * | 4/1987 | Emrich | 33/541 |
| 6,305,389 | B1 | * | 10/2001 | Bakken | 132/319 |
| 6,640,814 | B1 | * | 11/2003 | Burke | 132/319 |
| D677,004 | S | * | 2/2013 | Cole et al. | D28/92 |
| 2004/0107975 | A1 | * | 6/2004 | Bender | 132/319 |
| 2004/0231688 | A1 | * | 11/2004 | Thayer | 132/216 |

\* cited by examiner

*Primary Examiner* — Laura Martin
*Assistant Examiner* — Rhyan C Lange
(74) *Attorney, Agent, or Firm* — Richard L Miller

(57) ABSTRACT

An eyelash measuring device having: a ruler, a substantially eye shaped opening formed by an upper arch and a lower arch, and a graticule. The ruler is on the upper arch of the substantially eye-shaped opening and allows a user to measure an eyelash, and then set the measurement via the graticule. The eye shaped opening allows a user to gaze through the device to a mirror for measuring, and the ruler is printed in reverse so that when gazing in a mirror the type appears to be correctly oriented.

5 Claims, 5 Drawing Sheets

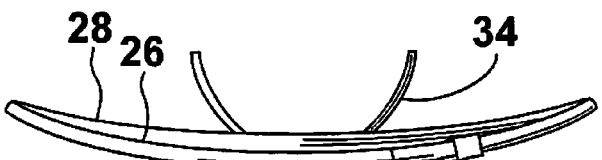
*Fig. 3*
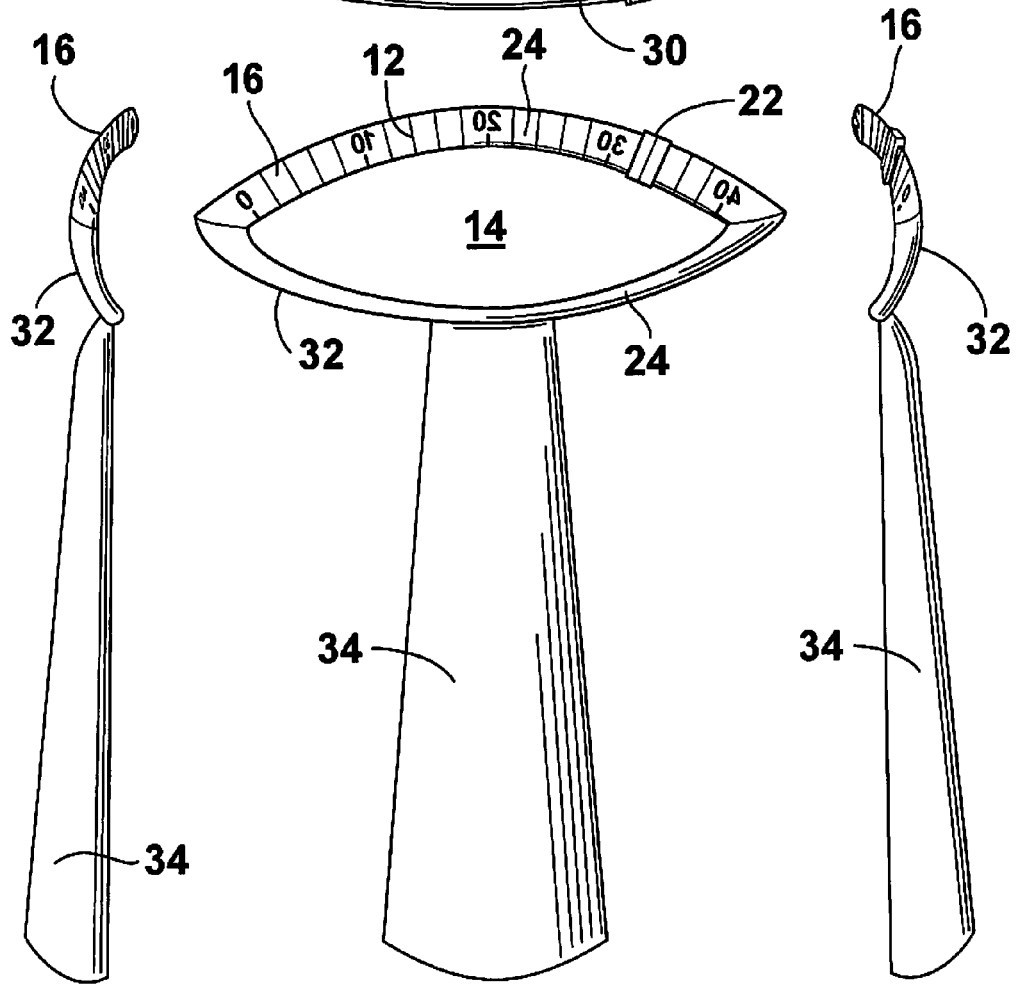
*Fig. 4*     *Fig. 5*     *Fig. 6*
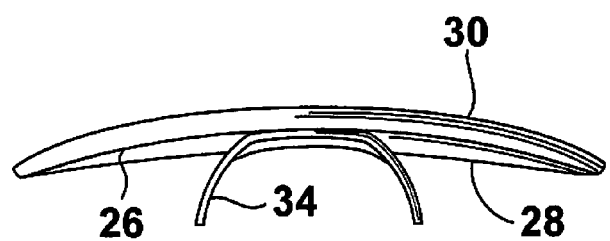
*Fig. 7*

EYELASH MEASURING DEVICE

BACKGROUND OF THE INVENTION

1. Field of the Invention

The present invention relates to a measuring device, and more particularly, an EYELASH MEASURING DEVICE.

2. Description of the Prior Art

Numerous innovations for eye-related measuring devices have been provided in the prior art that will be described. Even though these innovations may be suitable for the specific individual purposes to which they address, however, they differ from the present invention.

A FIRST EXAMPLE, U.S. Pat. No. 3,050,860, Published/Issued on Aug. 28, 1962, to Kosh teaches an instrument for measuring the vertical and horizontal dimensions of a rectangle circumscribing a lens.

A SECOND EXAMPLE, U.S. Pat. No. 3,200,823, Published/Issued on Aug. 17, 1965, to Sebastian teaches a device for imparting a selectable curvature and uniform spacing to lash hairs of artificial eyelashes to be used in manufacturing and maintaining such artificial eyelashes.

A THIRD EXAMPLE, U.S. Pat. No. 3,517,673, Published/Issued on Jun. 30, 1970, to Kim teaches a measuring device that permits a false eyelash to be accurately sized to complement the user's eye both as to shape and length. The trimmer allows a false eyelash to be cut accurately to size and shape. The measuring device is used manually by an individual to suit the individual's taste.

A FOURTH EXAMPLE, U.S. Pat. No. 3,557,653, Published/Issued on Jan. 26, 1971, to Kim teaches a measuring device that permits a false eyelash to be accurately sized to compliment the user's eye both as to shape and length. The trimmer allows a false eyelash to be cut accurately to size and shape. The measuring device is used manually by an individual to suit the individual's taste.

It is apparent now that numerous innovations for eye-related measuring devices have been provided in the prior art that adequate for various purposes. Furthermore, even though these innovations may be suitable for the specific individual purposes to which they address, accordingly, they would not be suitable for the purposes of the present invention as heretofore described.

SUMMARY OF THE INVENTION

AN OBJECT of the present invention is to provide an EYELASH MEASURING DEVICE that avoids the disadvantages of the prior art.

ANOTHER OBJECT of the present invention is to provide an EYELASH MEASURING DEVICE that is simple and inexpensive to manufacture.

STILL ANOTHER OBJECT of the present invention is to provide an EYELASH MEASURING DEVICE that is simple to use.

BRIEFLY STATED, STILL YET ANOTHER OBJECT of the present invention is to provide an EYELASH MEASURING DEVICE that allows for a compact and hand-held implementation.

The novel features which are considered characteristic of the present invention are set forth in the appended claims. The invention itself, however, both as to its construction and its method of operation, together with additional objects and advantages thereof, will be best understood from the following description of the specific embodiments when read and understood in connection with the accompanying drawing.

BRIEF DESCRIPTION OF THE DRAWING

The figures of the drawings are briefly described as follows:

FIG. 3 is a top plan view thereof, taken in the direction of arrow 3 in FIG. 2;

FIG. 4 is a side elevational view, taken in the direction of arrow 4 in FIG. 2;

FIG. 5 is an elevational view of an embodiment of the EYELASH MEASURING DEVICE intended for measuring the eyelash on a left eye;

FIG. 6 is a side elevational view, taken in the direction of arrow 6 in FIG. 2;

FIG. 7 is a bottom plan view thereof, taken in the direction of arrow 7 in FIG. 2;

Figure 1:
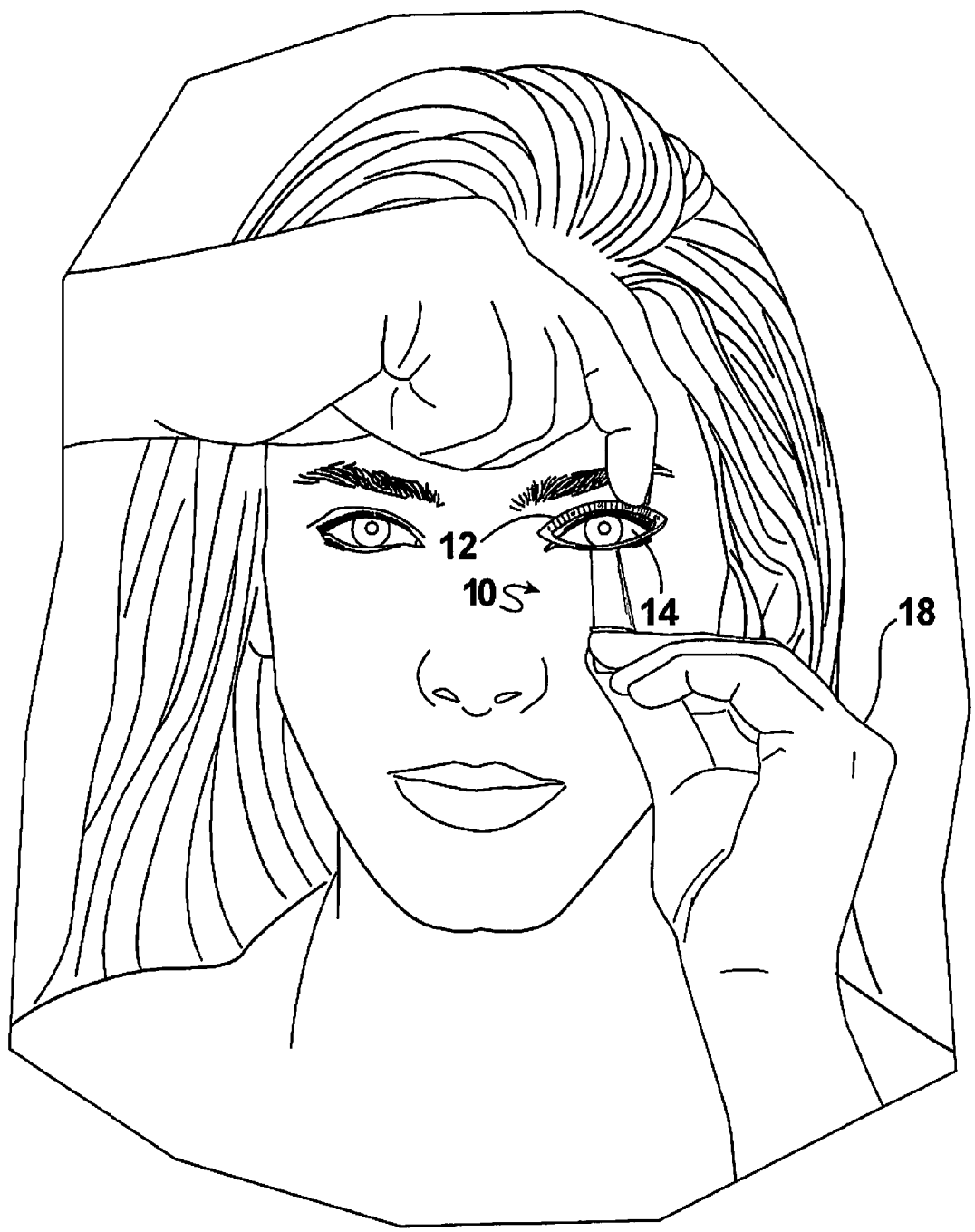
FIG. 1 is a diagrammatic front perspective view illustrating a person measuring the length of an eyelash on their left eye.
Figure 2:
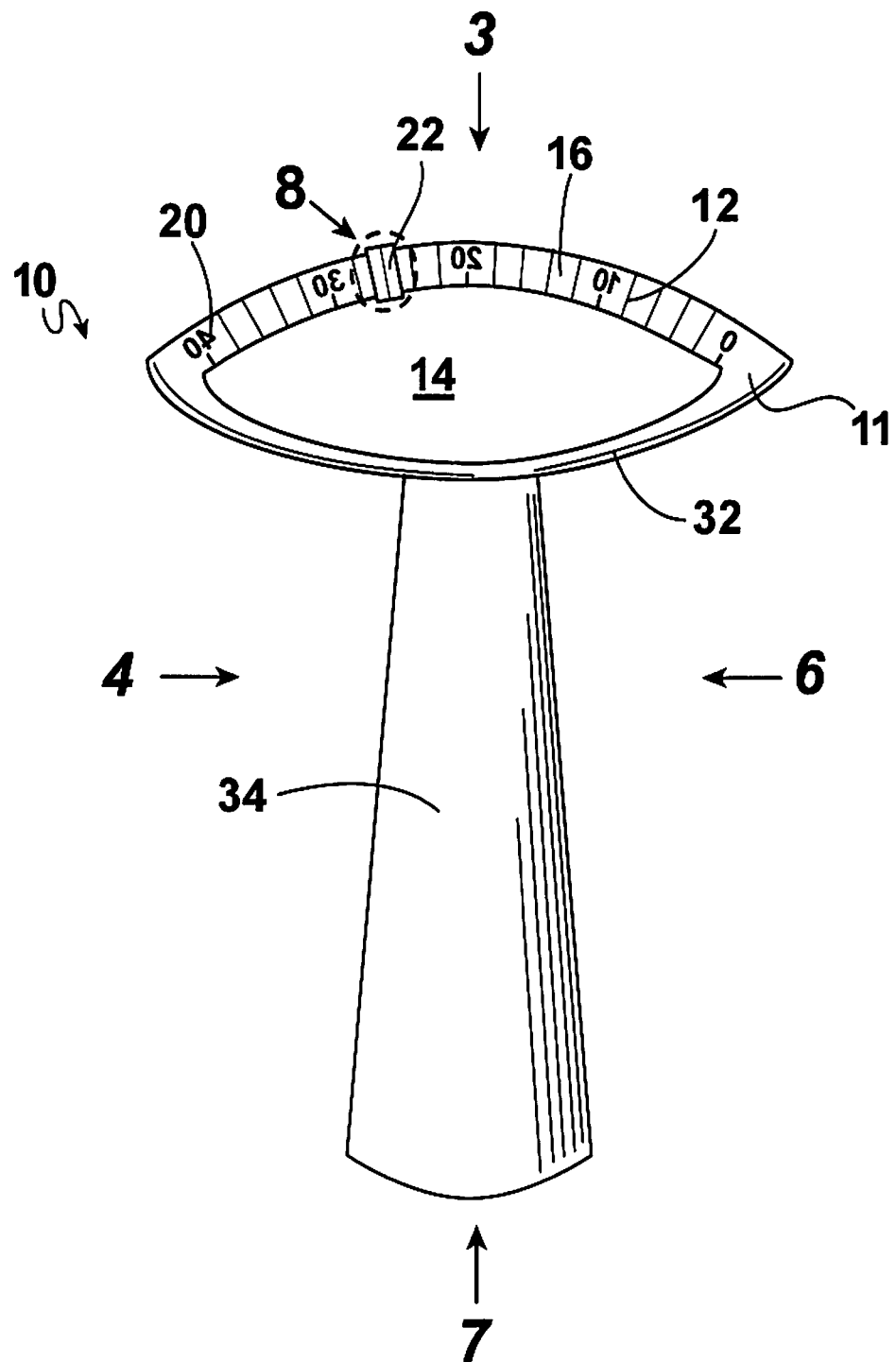
FIG. 2 is an elevational view of an embodiment of the EYELASH MEASURING DEVICE intended for measuring the eyelash on a right eye.
Figure 8:
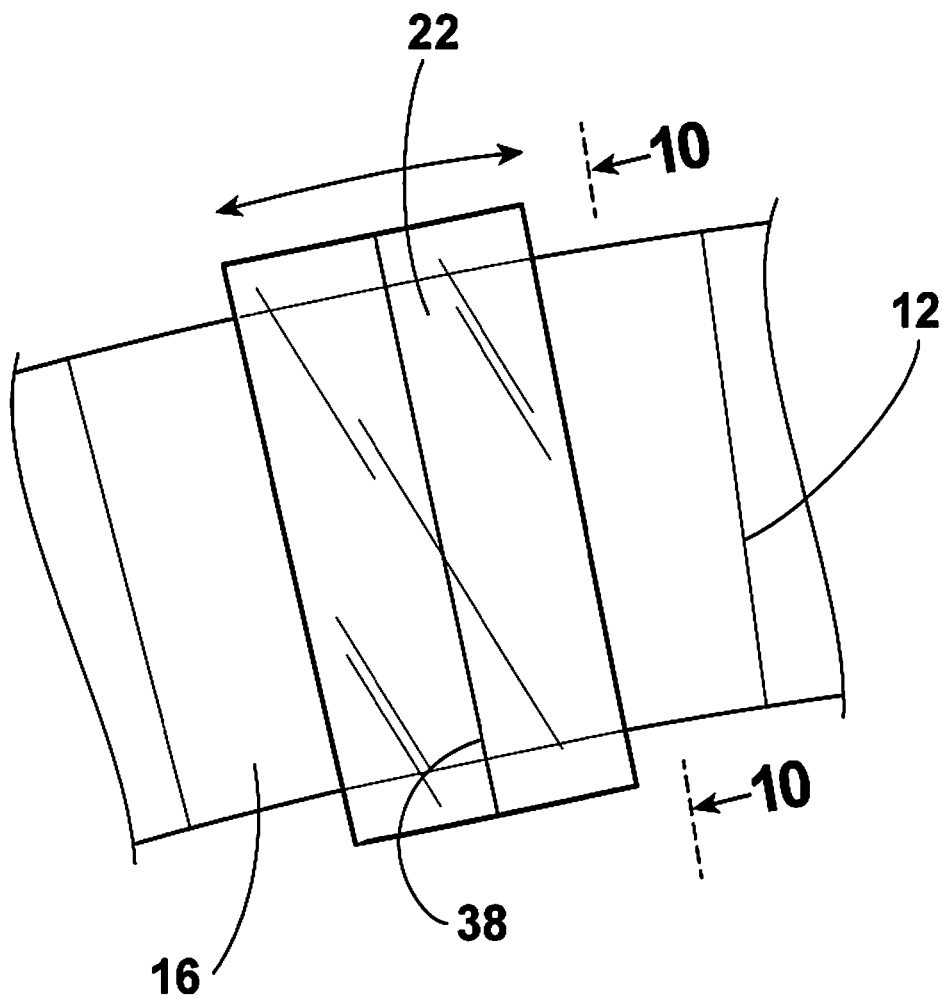
FIG. 8 is an enlarged view of the area enclosed in the dotted circle indicated by arrow 8 in FIG. 2, showing the sliding graticule in greater detail cooperating with a scale on an ocular window component.
Figure 9:
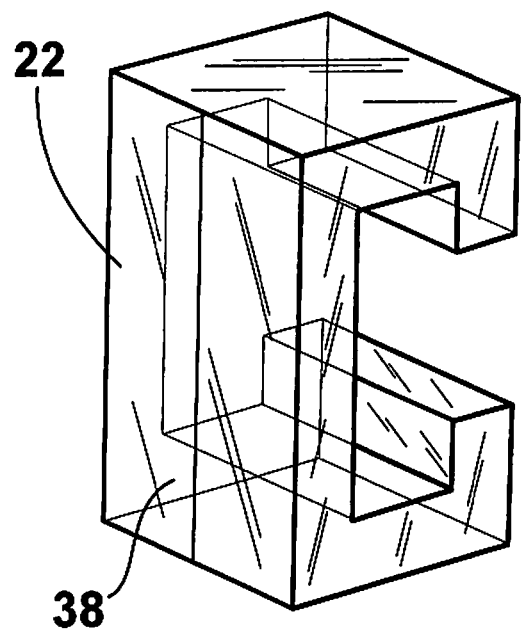
FIG. 9 is an enlarged diagrammatic perspective view illustrating sliding graticule per se.
Figure 10:
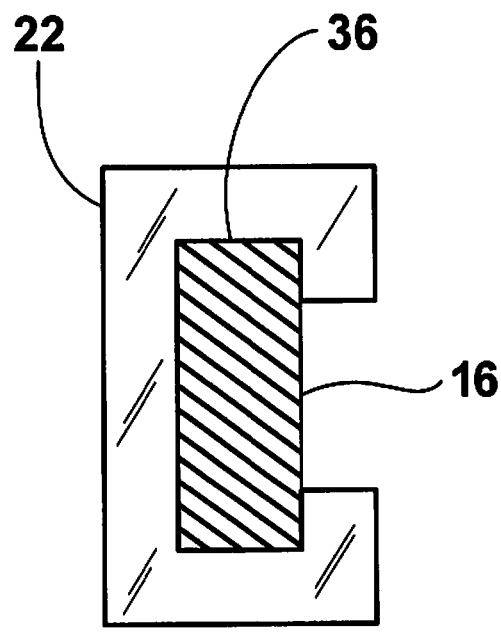
FIG. 10 is a cross sectional view on line 10-10 in FIG. 8.

A MARSHALING OF REFERENCE NUMERALS UTILIZED IN THE DRAWING 10 eyelash measuring device
11 substantially eye-shaped member
12 ruler
14 substantially eye-shaped opening of substantially eye-shaped member 11
16 upper arch of substantially eye-shaped opening 14
18 user
20 reverse printing of ruler 12
22 sliding graticule
24 front side of substantially eye-shaped opening 14
26 back side of substantially eye-shaped opening 14
28 concavity of back side 26 of substantially eye-shaped opening 14
30 convexity of front side 24 of substantially eye-shaped opening 14
32 lower arch of substantially eye-shaped opening 14
34 handle
36 encompassing of upper arch by sliding graticule 22
38 vertical line of sliding graticule 22

DETAILED DESCRIPTION OF THE PREFERRED EMBODIMENT

Referring now to the figures, in which like numerals indicate like parts, and particularly to FIG. 1, disclosed is an eyelash measuring device 10 which comprises a ruler 12 and a substantially eye-shaped member 11, which has a substantially eye-shaped opening 14.

Detailed Description of the Substantially Eye-Shaped Opening 14

Referring now to FIGS. 2-7, the substantially eye-shaped member 11 comprises an upper arch 16. The ruler 12 is printed on the upper arch 16. This allows a user 18 to measure his or her eye by placing of the ruler 12 in proximity to that user's 18 eye so that the upper arch 16 containing the ruler 12 is proximal to the eyelash of the user 18.

To further facilitate this, the ruler 12 is printed in reverse 20 on the upper arch 16. This allows for a user 18 to measure an eyelash by gazing through the substantially eye shaped opening 14 to a mirror, where the reverse printing 20 will then appear readable in the correct direction as a mirror image. A user then utilizes a sliding graticule 22 to keep the measurement spot, which graticule 22 will be discussed in greater detail below.

The substantially eye-shaped opening comprises a front side 24 and a back side 26. The ruler 12 is printed on the front side 24 of said substantially eye-shaped opening 14. This allows that the back side 26 abuts the user's eye with the ruler visible on the front side. The back side 26 is concave 28 with respect to a user's 18, and the front side 28 is correspondingly convex 30 with respect to the concavity 28 of the back side 26. This allows the device to better conform to the shape of a human eye. The ruler follows the upper arch 16 along its path (which includes the concavity 28 and convexity 30) just described, which facilitates measurement of what would otherwise be a very difficult area, since it is not a straight line in any of the three orthogonal dimensions.

The substantially eye-shaped opening 14 in a preferred construction also comprises a lower arch 32. The lower arch 32 depends from the upper arch 16 and combines with the upper arch to provide the eye-shaped opening 14. While other shapes could be used, a lower arch 32 is by far the simplest and most direct means of completing the eye-shaped opening.

Additionally, the preferred construction of the device 10 further comprises a handle 34 which depends from the lower arch, to facilitate holding of the device 10 by a user 18.

Detailed Description of the Sliding Graticule 22

To facilitate measurement and allow a user to keep a measurement made easily, a sliding graticule 22 is provided. The graticule 22 is for sliding along the upper arch 16. It allows a user to denote a measured position on the ruler 12 on the upper arch 16, which position would normally correspond to the end of an eyelash. To do this, the graticule 22 at least partially encompasses 36 the upper arch 16. Thus it can slide along the upper arch 16 without falling off.

To further facilitate measurement, a vertical line graticule 38 is utilized to allow easy correspondence of the graticule to a particular spot on the ruler 12.

Method of Using the Device 10

The preferred method of using the device is first placing the ruler 12 in proximity to a user's 18 eye so that the upper arch 16 is proximal to the eyelash of the user 18. Then, second, measuring said user's 18 eyelash by said user gazing through the substantially eye shaped opening 14 to a mirror, where the reverse printing 20 will then appear readable in the correct direction as a mirror image. This facilitates using the device with any common household mirror, and lets a user 18 adjust the distance at which the ruler 12 is read, which advantages it over prior art methods, particularly for users 18 who may be sight impaired at some distances such as nearsightedness or farsightedness. This is particularly useful in the case of an eyelash measuring device 10, since measuring an eyelash precludes the wearing of eyeglasses.

Accordingly a method of using an eyelash measuring device 10, is such that said eyelash measuring device 10 comprises a substantially eye shaped member 11 having a substantially eye shaped opening 14, which opening is formed by an upper arch 16 and a lower arch 32, and wherein a ruler 12 with reversed printing 20 is disposed on said upper arch 16, which method comprises the steps of:

Step 1: placing of the ruler 12 in proximity to a user's eye so that said upper arch 16 is proximal to the eyelash of the user 18;

Step 2: measuring said user's eyelash by said user gazing through the substantially eye shaped opening 14 to a mirror, where the reverse printing 20 will then appear readable in the correct direction as a mirror image;

Step 3: positioning a sliding graticule 22 at an end of an eyelash; and

Step 4: recording the measurement indicated on the ruler 12 by the sliding graticule 22.

It will be understood that each of the elements described above, or two or more together, may also find a useful application in other types of constructions differing from the types described above.

While the invention has been illustrated and described as embodiments of an EYELASH MEASURING DEVICE, accordingly it is not limited to the details shown, since it will be understood that various omissions, modifications, substitutions and changes in the forms and details of the device illustrated and its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute characteristics of the generic or specific aspects of this invention.

The invention claimed is:

1. An eyelash measuring device which comprises:
   a) a ruler;
   b) a substantially eye-shaped member;
   c) a sliding graticule; and
   d) a handle;
   wherein said ruler includes numerical indicia;
   wherein said substantially eye-shaped member comprises a substantially eye-shaped opening;
   wherein said substantially eye-shaped member comprises an upper arch;
   wherein said substantially eye-shaped opening is for gazing through;
   wherein said ruler is disposed on said upper arch;
   wherein said ruler is for measuring an eyelash;
   wherein said numerical indicia of said ruler is disposed in reverse so as to form reverse disposal;
   wherein said reverse disposal of said numerical indicia of said ruler is for facilitating reading said ruler in a mirror;
   wherein said graticule slides along said upper arch;
   wherein said graticule is for allowing a user to denote a measured position on said ruler;
   wherein said lower arch has a midpoint; and
   wherein said handle depends from said midpoint of said lower arch.

2. The device of claim 1 wherein said sliding graticule at least partially encompasses said upper arch.

3. The device of claim 1 wherein said substantially eye-shaped member comprises a front side and a back side; and
   wherein said ruler is disposed on said front side of said substantially eye shaped opening.

4. The device of claim 3 wherein said back side is concave with respect to a user's eye; and
   wherein said front side is correspondingly convex to said concavity of said back side.

5. The device of claim 4 wherein said eye shaped member further comprises a lower arch;
   wherein said lower arch depends from said upper arch; and
   wherein said upper arch and said lower arch combine to provide said eye-shaped opening.

* * * * *